United States Patent [19]

Shioyama

[11] 4,260,845
[45] Apr. 7, 1981

[54] ALCOHOL DEHYDRATION EMPLOYING A ZINC ALUMINATE CATALYST

[75] Inventor: Tod K. Shioyama, Bartlesville, Okla.

[73] Assignee: Phillips Petroleum Company, Bartlesville, Okla.

[21] Appl. No.: 113,948

[22] Filed: Jan. 21, 1980

[51] Int. Cl.³ .............................................. C07C 1/00
[52] U.S. Cl. ................................................... 585/640
[58] Field of Search ........................................ 585/640

[56] References Cited

U.S. PATENT DOCUMENTS

| | | | |
|---|---|---|---|
| 1,859,529 | 1/1933 | Taylor et al. | 585/640 |
| 2,963,524 | 12/1960 | Shackelford et al. | 585/640 |
| 3,668,151 | 6/1972 | Walker | 252/466 |

OTHER PUBLICATIONS

Kirk-Othmer Ency. of Chem. Tech., 2nd Ed., vol. 14, 1967, pp. 325, 326.

Primary Examiner—Curtis R. Davis

[57] ABSTRACT

A zinc aluminate dehydration catalyst, suitably activated, as by heating in air, is employed to dehydrate a saturated alcohol to produce an olefin.

15 Claims, 1 Drawing Figure

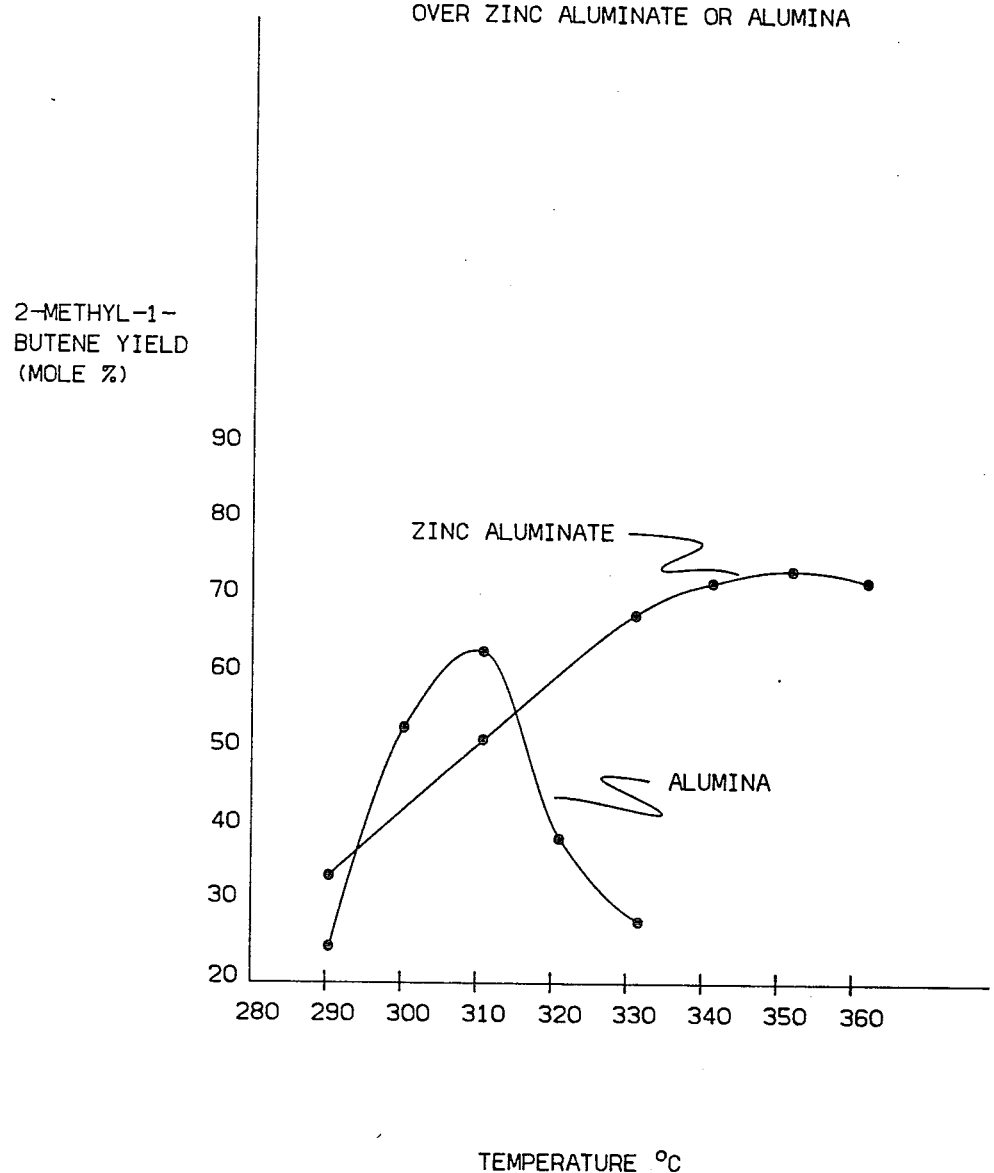

ALCOHOL DEHYDRATION EMPLOYING A ZINC ALUMINATE CATALYST

BRIEF SUMMARY OF THE INVENTION

A saturated alcohol is dehydrated to an olefin employing a zinc aluminate dehydration catalyst having an approximate molar ratio of zinc oxide to aluminum oxide of one, the catalyst having been heated to activate the same.

DETAILED DESCRIPTION

This invention relates to the dehydration of an alcohol. It also relates to the production of an olefin. In one of its aspects, the invention relates to the dehydration of an alcohol to form an olefin employing a contact mass or dehydration catalyst especially suited to this purpose.

In one of its concepts the invention provides a process for the dehydration of an alcohol to form an olefin by subjecting the same to dehydrating conditions in the presence of a zinc aluminate dehydration catalyst, the catalyst having an approximate molar ratio of ZnO to $Al_2O_3$ of one, the catalyst having been heated in air for a sufficient time and at a sufficient temperature to form a catalytically active zinc aluminate suitable for said dehydration.

Several catalysts, including alumina, thoria, and strong mineral acids such as sulfuric acid, have been used for the dehydration of alcohols to olefins. While in some cases these catalysts are satisfactory, in other cases undesirable side reactions such as isomerization of the olefin to another, frequently less desirable, isomer occur. In some instances, optimum olefin yields are obtained only in a narrow temperature range which can be difficult to maintain in a large scale dehydration.

U.S. Pat. No. 2,963,524 issued Dec. 6, 1960, discloses so called "promoted" dehydration catalysts which comprise a silica, silica-alumina or alumina base and a minor portion (0.5 to 10 percent by weight) of a metal oxide, such as the oxides of thorium, iron, zinc, chromium, barium, copper, nickel, and cesium, stated to be useful in the invention there disclosed which is the making of 1,3,5,-hexatriene by dehydration of 1,4-hexadiene-3-ol.

I have now discovered that a zinc aluminate dehydration catalyst prepared as herein described and having the characteristics as herein described, employed as herein described, is preeminently useful with good selectivity to dehydrate an alcohol as herein described to an olefin.

It is an object of this invention to dehydrate an alcohol. It is another object of the invention to produce an olefin. It is a further object of the invention to provide a contact mass or dehydration catalyst suitable to dehydrate a dehydratable saturated alcohol to an olefin.

Other aspects, concepts, objects and the several advantages of the invention are apparent from a study of this disclosure, the drawing, and the appended claims.

According to the present invention, the dehydration to an olefin of a dehydratable saturated alcohol is effected by subjecting the alcohol to dehydrating conditions in the presence of a zinc aluminate dehydration catalyst in which the ratio of ZnO to $Al_2O_3$ is equal to approximately one, the catalyst having prepared by a process including the heating as in air for a sufficient time at a sufficient temperature to form a catalytically, active zinc aluminate suitable for said dehydration.

The zinc aluminate catalyst utilized according to the present invention is prepared by mixing nearly equimolar portions of alumina ($Al_2O_3$) and zinc oxide (ZnO), producing the desired catalyst shape, and calcining the mixture.

The preparation of the zinc aluminate can be carried out by any suitable method which yields a catalytically active zinc aluminate. One useful preparation is described in U.S. Pat. No. 3,668,151 for the preparation of a high strength zinc aluminate catalyst pellet.

The zinc oxide (ZnO) used for the preparation of zinc aluminate can be any particulate ZnO having an average particle diameter in the range from about 0.1 to about 1,000 microns; however, entirely satisfactory results are obtained when the ZnO average particle diameter is in the range of about 40 to about 900 microns.

The alumina ($Al_2O_3$) used for the preparation of zinc aluminate can be any particulate alumina that is predominantly in the gamma ($\gamma$) crystal form as determined by X-ray crystallography or that can be transformed during the catalyst preparation step to the $\gamma$ crystal form and wherein the average particle diameter is in the range from about 0.01 to about 1000 microns. For reasons of availability, the preferred average particle diameter is in the range of from about 0.025 to about 900 microns. Examples of suitable aluminas include those sold commercially by the Conoco Chemicals Division of Continental Oil Co., Houston, Texas, under the trademark CATAPAL and flame-hydrolyzed $Al_2O_3$ made by the hydrolysis of aluminum chloride in a flame process such as the $Al_2O_3$ sold commercially by the Cabot Corporation, Boston, Mass., under the trademark ALON. The CATAPAL aluminas are $\alpha$-alumina monohydrates which are converted during the calcination step to $\gamma$-aluminas and the ALON is predominantly in the gamma crystalline form.

The ZnO and the $Al_2O_3$ are mixed in approximately equal molar ratios, e.g., together in a molar ratio of ZnO to $Al_2O_3$ of from about 1/0.95 to about 1/1.1. The two materials can be mixed in any manner that provides satisfactory admixing such as a ball mixer or a ball mill. Deionized water can be used to facilitate admixing if desired.

The ZnO-$Al_2O_3$ mixture can be dried prior to processing to the desired physical form, e.g., pelletizing, by any drying technique that will result in a sufficiently dry product to be useful in the subsequent steps. For example, deionized water used as a wetting agent can be removed by drying at about 100° C. for about 16 hours.

The admixture can be advantageously converted to the desired physical form such as pellets, extrudates, spheres, granules, and the like using techniques known in the art. If desired, various lubricants and other processing aids may be added. The formed particles should generally have an average particle diameter in the range from about 0.0059 inch (0.15 mm) to about ½ inch (12.7 mm) and preferably in the range from about 1/32 inch (0.79 mm) to about ¼ inch (6.35 mm). The lower limit on the particle size in a continuous dehydration process is determined by the formation of excessive pressure drop across the catalyst bed. The larger particle size limit for a continuous process is determined by the tendency to develop excessive channeling between the larger particles.

The formed particles are calcined by heating the particles in air for a sufficient time and at a sufficient temperature to form a catalytically active zinc aluminate. Broadly the calcination can be carried out from about 700° to about 1400° C., preferably from about 800° to about 1200° C. for about 0.1 to about 30 hours, preferably for about 1 to about 20 hours.

Zinc aluminates useful for the dehydration of alcohols generally have surface areas in the range of about 20 to about 200 m²/g, pore volumes in the range of about 0.4 to about 0.6 ml/g, and bulk densities in the range of about 0.6 to about 1.3 g/ml. The surface area determinations are by the B.E.T. method using nitrogen adsorption and the pore volume determinations are by water adsorption.

Thus, the basic steps in the formation of the zinc aluminate dehydration catalyst are combining ZnO and Al₂O₃, forming particles of the desired size and shape, and calcining the particles. Obviously, many variants and other steps, some are noted above, will be apparent to those skilled in the art.

The alcohol reactants useful in the catalytic dehydration process of the present invention are dehydratable alcohols generally described as saturated alcohols which contain from 2 to about 25 carbon atoms per molecule which can be represented by the following general formula I;

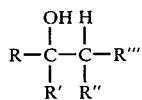

I wherein each of R, R', R", and R''' is independently chosen from a group consisting of hydrogen, alkyl radicals, cycloalkyl radicals, said radicals contain from 1 to about 23 carbon atoms per radical, any of said alkyl or cycloalkyl radicals can contain aryl or substituted aryl radicals with the substituents being one or more or a mixture of alkyl or alkoxy radicals and with the limitation that said aryl or substituted aryl radicals must be located at least two carbon atoms from the alcohol oxygen, and any two of R, R', R", and R''' can be combined to form a mono- or bicyclic system with the limitation that any cyclic ring bearing an alcohol group must contain at least 4 carbon atoms in the ring.

A presently preferred class of alcohols for use in the process of this invention contains from 5 up to about 25 carbon atoms per molecule and can be represented by the following general formula II;

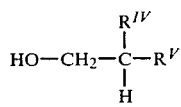

II wherein each of $R^{IV}$ and $R^V$ is independently chosen from a group consisting of alkyl radicals containing from 1 to about 20 carbon atoms per radical and wherein $R^{IV}$ and $R^V$ can be taken together to form a mono- or bicyclic system having at least 4 carbon atoms in a ring bearing an alcohol group.

The use of the present invention with the preferred group of alcohols is of particular value because these alcohols in the presence of alumina catalysts frequently produce relatively low yields of the terminal olefin due to isomerization of the terminal to the internal olefin whereas zinc aluminate produces a much higher yield of the terminal olefin. In addition, the maximum yields of the terminal olefins with alumina are obtained in a relatively narrow temperature range, whereas the zinc aluminate produces the high yields of terminal olefin over a much wider temperature range which reduces the requirement for very accurate temperature control which is difficult to accomplish on a large scale.

Specific examples of suitable alcohols include:

| | | |
|---|---|---|
| ethanol | 1-decanol | cyclodocosanol |
| 1-propanol | 1-undecanol | 4-methyl-2-pentanol |
| 2-propanol | 1-dodecanol | 5,5-dimethyl-1-hexanol |
| 1-butanol | 1-tridecanol | 5-phenyl-1-pentanol |
| 2-butanol | 1-tetradecanol | 8-phenyl-2-octanol |
| 1-pentanol | 2-tetradecanol | 2-methyl-2-pentanol |
| 2-pentanol | 1-hexadecanol | 1-methyl-1-cyclohexanol |
| 3-pentanol | 1-octadecanol | 2-methyl-1-cyclohexanol |
| 3-methyl-1-butanol | | bicyclo[2.2.2]octan-2-ol |
| 1-hexanol | 1-eicosanol | bicyclo[3.2.0]hepten-3-ol |
| 2-hexanol | 1-docosanol | bicyclo[2.2.1]heptan-2-ol |
| 3-hexanol | 1-pentacosanol | |
| 1-heptanol | cyclobutanol | |
| 1-octanol | cyclopentanol | |
| 2-octanol | cyclohexanol | |
| 1-nonanol | cyclooctanol | |
| 2-nonanol | cyclododecanol | | and the like.

Specific examples of the presently preferred alcohols include:

| | |
|---|---|
| 2-methyl-1-butanol | 2-methyl-1-docosanol |
| 2-ethyl-1-butanol | cyclobutylmethanol |
| 2-methyl-1-pentanol | cyclopentylmethanol |
| 2-ethyl-1-hexanol | cyclohexylmethanol |
| 2-methyl-1-decanol | cyclotetradecylmethanol |
| 2-ethyl-1-octadecanol | bicyclo[2.2.1]hept-2-ylmethanol |
| 2-methyl-1-eicosanol | bicyclo[2.2.2.]oct-2-ylmethanol | and the like

The olefinic products from the zinc aluminate catalyzed dehydration of the alcohols of general formula I can be represented by the following general formula III;

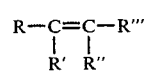

III wherein the R, R', R", and R''' have the previously stated meanings. Although some small amount of isomeric olefins will commonly be present, primary alcohols will yield predominantly terminal olefins and secondary or tertiary alcohols will yield predominantly internal olefins. As in most dehydrations, the order of preference of olefin formation is tetrasubstituted->trisubstituted->disubstituted->monosubstituted.

When cis- or trans-olefins can be formed, generally, a mixture is found with cis-predominating.

The dehydration of alcohols of general formula II with zinc aluminate forms products which can be represented by the following general formula IV;

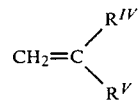

IV wherein $R^{IV}$ and $R^V$ have the previously stated significance. Although some isomeric olefin will usually be present, the quantities of isomers will be less than when other catalysts such as aluminas are used.

Specific examples of the dehydration of alcohols of formula I include the conversion of ethanol to ethylene, 1-propanol to propene, 2-propanol to propene, 1-butanol to 1-butene, 2-butanol to 2-butene, 1-pentanol to 1-pentene, 2-pentanol to 2-pentene, 3-pentanol to 2-pentene, 3-methyl-1-butanol to 3-methyl-1-butene, 1-tetradecanol to 1-tetradecene, 1-docosanol to 1-docosene, cyclobutanol to cyclobutene, cyclohexanol to cyclohexene, 5-phenyl-1-pentanol to 5-phenyl-1-pentene, 2-methyl-1-cyclohexanol to 1-methyl-1-cyclohexene, and bicyclo[2.2.1]heptan-2-ol to bicyclo[2.2.1]hept-2-ene. Both cis- and trans-isomers will be formed when possible.

Specific examples of the dehydration of alcohols of the general formula II include the dehydration of 2-methyl-1-butanol to 2-methyl-1-butene, 2-ethyl-1-butanol to 2-ethyl-1-butene, 2-methyl-1-pentanol to 2-methyl-1-pentene, 2-ethyl-1-hexanol to 2-ethyl-1-hexene, 2-methyl-1-decanol to 2-methyl-1-decene, cyclobutylmethanol to methylenecyclobutane, cyclohexylmethanol to methylenecyclohexane, and bicyclo[2.2.1]hept-2-ylmethanol to 2-methylenebicyclo[2.2.1]heptane.

The dehydration reaction is ordinarily carried out by bringing the alcohol into contact with the zinc aluminate catalyst under suitable reaction conditions. Any suitable mode of contact using any suitable type of reactor can be used. Continuous operation using a fixed bed reactor is the mode presently preferred.

The dehydration reaction of this invention is carried out broadly between about 200° and about 600° C., preferably between about 250° and about 450° C. At temperatures below about 200° C., the dehydration reaction normally is unacceptably slow, while at temperatures above about 600° C., side reactions, such as ether formation, are frequently observed. The optimum temperature range is dependent of the particular alcohol, catalyst preparation, and type of reactor employed and can be readily determined by a few well-chosen experiments.

The dehydration reaction can be carried out at pressures from about 0.5 atmospheres to about 1000 psig., but preferably is carried out between atmospheric pressure to about 50 psig. The reaction will generally be carried out at a weight hourly space velocity (WHSV) of about 0.05 to about 15, preferably about 0.2 to about 5 grams of alcohol feed per gram of catalyst per hour.

Although not required, in a currently preferred mode of operation a diluent such as nitrogen, argon, helium, and the like, that does not adversely affect the dehydration reaction is included in the alcohol feed stream. The diluent can be present at a level of about 1 to about 500 ml of diluent per g. of alcohol, preferably from about 10 to about 300 ml of diluent per g. of alcohol.

After leaving the reaction zone, the reaction mixture, which usually contains water, any unconverted alcohol, and at least one olefin, can be subjected to conventional separation means, such as fractional distillation, to isolate and recover the desired olefinic product. The unconverted alcohol can be recycled to the reaction zone, if desired.

The olefinic products of the dehydration process of this invention, for the most part, have established utility as precursors of polymers. For example, ethylene, propylene, and 1-butene are used to form polymers useful as plastic containers, films, cable coatings, pipe, and the like. In addition, other olefins can be used as the third component of ethylene-propylene terpolymers useful as synthetic elastomers. 2-Methyl-1-butene and 3-methyl-1-butene in the form of copolymers with other olefins have been found to be useful as adhesives, coatings, lubricants, and tackifiers for rubber adhesives.

The following examples representative of the work done were carried out in a ⅝" (16 mm) diameter ×20" (508 mm) length stainless steel continuous reactor fitted with electrical heater and temperature sensors. The reactor contained a quantity of glass beads on either side of the ~14" (356 mm) catalyst bed, with the glass beads preceding the catalyst bed acting as a preheat zone to insure vaporization of the feed.

The alcohols and aluminas used in the examples were commercial materials which were not purified further. The zinc aluminate catalysts, unless otherwise stated, were prepared by calcining mixtures (about 1:1 mole ratio) of zinc oxide (40 to 100μ diameter) and CATAPAL - an α-alumina monohydrate (more than 85% is less than 1000μ in diameter) which is converted to γ-alumina during the calcining step—at about 1000° C. The surface areas were determined by the B.E.T. method using nitrogen adsorption and the pore volumes were determined by water adsorption.

A mixture of nitrogen (3.2 l/hour) and the alcohol were fed to the preheated reactor. The reactor effluent was passed through a warm flask to trap water and unreacted alcohol and then through two cold traps to collect the olefins. The dehydration reactions were carried out for one hour and samples of the olefin products were collected for analysis by gas liquid chromatography (glc) for selectivity of the reacted alcohol to a specific olefin. The conversion of the alcohol to products was determined from the weights of the various traps. Yields to a specific olefin were calculated by conversion x selectivity.

The reaction products were identified by glc-mass spectra, and by glc comparison with known materials.

EXAMPLE I

Two runs were carried out according to the process of the instant invention for the dehydration of 2-methyl-1-butanol to 2-methyl-1-butene. The catalyst in each run was a zinc aluminate coded R8300 from Harshaw Chemical Company, Cleveland, Ohio. The zinc aluminate catalyst was in the form of a 1/16" extrudate and had a surface area of 78 m²/g, a pore volume of 0.48 ml/g, and a bulk density of 1.06 g/ml.

Run 1 was carried out at atmospheric pressure and run 2 was carried out at a pressure of 30 psig. The 2-methyl-1-butanol was introduced at a rate of 29 g/hr. in both runs. The weight hourly space velocity for runs 1 and 2 were 0.44 and 0.46 respectively. Table I presents the results of the runs at several different temperatures.

|       | Reaction Temp., °C. | Conv., % | Selectivity To 2-Methyl-1-butene, % | 2-Methyl-1-butene Yield, mole % |
|-------|---------------------|----------|-------------------------------------|-------------------------------|
| Run 1 | 270 | 13 | 85 | 11 |
|       | 290 | 40 | 86 | 34 |
|       | 310 | 62 | 84 | 52 |
|       | 330 | 81 | 83 | 67 |
|       | 340 | 88 | 81 | 71 |
|       | 350 | 94 | 78 | 73 |
|       | 360 | 94 | 77 | 72 |
| Run 2 | 300 | 73 | 79 | 58 |
|       | 310 | 78 | 78 | 61 |
|       | 330 | 87 | 74 | 64 |
|       | 350 | 94 | 71 | 67 |
|       | 360 | 96 | 68 | 65 |

| Reaction Temp., °C. | Conv., % | Selectivity To 2-Methyl-1-butene, % | 2-Methyl-1-butene Yield, mole % |
|---|---|---|---|
| 370 | 94 | 68 | 64 |

The results of runs 1 and 2 demonstrate the process of the instant invention for the dehydration of 2-methyl-1-butanol to 2-methyl-1-butene in the presence of zinc aluminate. As the reaction temperature increases, the conversion of the 2-methyl-1-butanol increases and the selectivity to 2-methyl-1-butene decreases. The use of higher pressure in run 2 resulted in an increase in conversion and a slight decrease in selectivity to 2-methyl-1-butene compared with run 1 which used atmospheric pressure. In both runs, a high yield of 2-methyl-1-butene was obtained over a relatively wide temperature range. The yields from run 1 are plotted in the drawing along with the corresponding yields from run 3 of Example II which used an alumina catalyst. The zinc aluminate catalyst gave a good yield of 2-methyl-1-butene from about 330° to about 360° C., while the alumina catalyst gave the highest yield at about 310° C. Zinc aluminate would therefore have a considerable advantage over alumina in a large scale dehydration process because temperature variations would have less effect on yield than with alumina.

EXAMPLE II

Several control runs were carried out using aluminas and base-treated aluminas as the catalyst for the dehydration of 2-methyl-1-butanol to 2-methyl-1-butene. Runs 3 and 4 used a United T2275 alumina in the form 8 to 14 mesh granules from United Catalyst Inc. and a Kaiser S-201 alumina in the form of ⅛″ diameter spheres from Kaiser Chemicals respectively. Runs 5 and 6 used a base treated (0.25 weight % KOH) Kaiser A-2 alumina. Run 6 was carried out at a pressure of 30 psig while the other runs were at atmospheric pressure. The results of these runs are presented in Table II.

TABLE II

| | WHSV | Temp., °C. | Conv., % | Selectivity To 2-Methyl-1-butene, % | 2-Methyl-1-butene Yield, Mole % |
|---|---|---|---|---|---|
| Run 3 | 1.14 | 290 | 31 | 80 | 25 |
| | | 300 | 67 | 79 | 53 |
| | | 310 | 98 | 64 | 63 |
| | | 320 | 99 | 39 | 39 |
| | | 340 | 99 | 28 | 28 |
| Run 4 | 0.64 | 280 | 6 | 93 | 6 |
| | | 300 | 15 | 93 | 14 |
| | | 320 | 44 | 88 | 39 |
| | | 340 | 92 | 70 | 64 |
| | | 350 | 100 | 51 | 51 |
| | | 360 | 100 | 43 | 43 |
| Run 5 | 0.85 | 330 | 14 | 93 | 13 |
| | | 350 | 52 | 88 | 46 |
| | | 360 | 72 | 84 | 60 |
| | | 370 | 94 | 82 | 77 |
| Run 6 | 0.75 | 300 | 7 | 93 | 6 |
| | | 330 | 17 | 91 | 15 |
| | | 350 | 49 | 89 | 43 |
| | | 360 | 83 | 76 | 63 |
| | | 370 | 94 | 71 | 67 |
| | | 380 | 95 | 64 | 61 |
| | | 400 | 94 | 41 | 38 |

The results described in Table II show that the dehydration of 2-methyl-1-butanol in the presence of alumina catalysts (run 3 and 4) gives a relatively low overall yield of 2-methyl-1-butene and a very narrow range of temperatures for the higher yields. Although the base-treated aluminas (runs 5 and 6) are an improvement over the untreated aluminas, a comparison with the results in Table I for runs using zinc aluminate shows that with the base-treated alumina, higher reaction temperatures are required and the higher yields were obtained only in a fairly narrow temperature range.

EXAMPLE III

Several more control runs were carried out to demonstrate that simple mixtures of zinc oxide and alumina are not as effective as the zinc aluminate catalyst for alcohol dehydration. Each run involved the dehydration of 2-methyl-1-butanol to 2-methyl-1-butene in the presence of one of several mixtures of zinc oxide (as a ⅛ inch diameter extrudate) and a base-treated (0.25 weight % KOH) Kaiser A-2 alumina (as ⅛″ diameter spheres). Each run was carried out at 30 psig of nitrogen pressure and at several different reaction temperatures. These results are presented in Table III.

TABLE III

| | ZnO/Al₂O₃ Wt. Ratio | Temp., °C. | Conv. % | Selectivity To 2-Methyl-1-butene % | 2-Methyl-1-butene Yield, mole % |
|---|---|---|---|---|---|
| Run 7ᵃ | 50/50 | 350 | 22 | 90 | 20 |
| | | 380 | 33 | 88 | 29 |
| | | 400 | 54 | 86 | 46 |
| Run 8ᵇ | 75/25 | 350 | 22 | 90 | 20 |
| | | 370 | 29 | 89 | 26 |
| | | 390 | 46 | 87 | 40 |
| | | 400 | 60 | 84 | 50 |
| | | 410 | 70 | 82 | 57 |
| Run 9ᶜ | 90/10 | 350 | 30 | 90 | 27 |
| | | 370 | 43 | 89 | 38 |
| | | 390 | 62 | 85 | 53 |
| | | 400 | 72 | 82 | 59 |
| | | 410 | 73 | 79 | 58 |

ᵃWHSV = 0.56
ᵇWHSV = 0.58
ᶜWHSV = 0.65

The results of these runs show that mixtures of ZnO and Al₂O₃ are much less effective for alcohol dehydration than the zinc aluminate catalyst described in Example I.

EXAMPLE IV

Several more runs were carried out to demonstrate the process of the instant invention for the dehydration of several different alcohols. In each of runs 10, 11, 12, and 13, the catalyst was the Harshaw zinc aluminate catalyst described in Example I. The alcohols were 1-pentanol (run 10), 2-pentanol (run 11), 3-methyl-1-butanol (run 12), and cyclohexanol (run 13). Each run was carried out at atmospheric pressure and at several different temperatures. The results of these runs are presented in Tables IV, V, VI, and VII.

TABLE IV

| | Temp., °C. | Conversion, % | Selectivity To 1-Pentene, % |
|---|---|---|---|
| Run 10ᵃ | 280 | 18 | 98 |
| | 300 | 41 | 97 |
| | 320 | 67 | 96 |
| | 330 | 48 | 96 |
| | 340 | 62 | 96 |
| | 350 | 79 | 96 |

TABLE IV-continued

| Temp., °C. | Conversion, % | Selectivity To 1-Pentene, % |
|---|---|---|
| 360 | 93 | 95 |

[a]1-Pentanol feed rate = 30.1 g/hr.
WHSV = 0.53

TABLE V

| | Temp., °C. | Conversion, % | Selectivity To 2-Pentene, % |
|---|---|---|---|
| Run 11[a] | 230 | 58 | 60 |
| | 240 | 83 | 63 |
| | 250 | 99 | 65 |

[a]2-Pentanol feed rate = 27.7 g/hr.
WHSV = 0.50

TABLE VI

| | Temp., °C. | Conversion, % | Selectivity To 3-Methyl-1-butene, % |
|---|---|---|---|
| Run 12[a] | 373 | 94 | 94 |
| | 381 | 96 | 95 |

[a]3-Methyl-1-butanol feed rate = 28.6 g/hr.
WHSV = 0.45

TABLE VII

| | Temp., °C. | Conversion, % | Selectivity To Cyclohexene, % |
|---|---|---|---|
| Run 13[a] | 300 | 69 | 100 |
| | 315 | 93 | 99 |
| | 315 | 94 | 100 |

[a]Cyclohexanol feed rate = 31.5 g/hr.
WHSV = 0.94

These results show that the zinc aluminate catalyst of the present invention is suitable for the dehydration of 1-pentanol to 1-pentene, 2-pentanol to 2-pentene, 3-methyl-1-butanol to 3-methyl-1-butene, and cyclohexanol to cyclohexene.

EXAMPLE V

Two runs were carried out to deomonstrate the importance of the calcination temperature used during the zinc aluminate preparation. In both runs, 2-methyl-1-butanol was dehydrated to 2-methyl-1-butene at atmospheric pressure. The zinc aluminate in run 14 was calcined at about 700° C., while the zinc aluminate in run 15 was calcined at about 1000° C. Both zinc aluminates were in the form of 1/16" extrudates and were identical in zinc oxide and alumina components and preparation procedure other than the calcination temperature. The results of the two runs are presented in Table VIII.

TABLE VIII

| | Temp., °C. | Conversion, % | Selectivity To 2-Methyl-1-butene, % |
|---|---|---|---|
| Run 14[a] | 300 | 35 | 88 |
| | 320 | 50 | 87 |
| | 340 | 64 | 86 |
| | 360 | 78 | 84 |
| | 400 | 94 | 78 |
| Run 15[b] | 300 | 43 | 87 |
| | 330 | 72 | 84 |
| | 350 | 86 | 82 |
| | 370 | 100 | 80 |

[a]2-Methyl-1-butanol feed rate = 30 g/hr.
WHSV = 0.91
[b]2-Methyl-1-butanol feed rate = 29.5 g/hr.
WHSV = 0.55

These results show that higher conversions are obtained at a given reaction temperature for a zinc aluminate calcined at 1000° C. (run 15) than with a zinc aluminate calcined at 700° C.

EXAMPLE VI

A control run was carried out to demonstrate the influence of an excess of ZnO in the ZnO/Al$_2$O$_3$ mixture used for the preparation of a zinc aluminate. 2-Methyl-1-butanol was dehydrated to 2-methyl-1-butene in the presence of a zinc aluminate prepared from a 1/0.93 mole ratio of ZnO and Al$_2$O$_3$. The catalyst was in the form of a 1/16 inch extrudate. The dehydration results are shown in Table IX.

TABLE IX

| | Temp., °C. | Conversion, % | Selectivity To 2-Methyl-1-butene, % |
|---|---|---|---|
| Run 16[a] | 310 | 17 | 83 |
| | 330 | 17 | 78 |
| | 360 | 23 | 71 |
| | 380 | 35 | 56 |

[a]WHSV = 0.55

The results of this run are significantly worse than the results in run 1 of Example I which used a zinc aluminate catalyst prepared from a 1:1 mole ratio of ZnO to Al$_2$O$_3$. The alcohol conversions are low even at 380° C. and the selectivities to 2-methyl-1-butene are decreasing sharply at the higher temperatures.

Reasonable variation and modification are possible within the scope of the foregoing disclosure, drawing, and the appended claims to the invention the essence of which is that a dehydratable saturated alcohol has been dehydrated with good selectivity to produce an olefin employing a zinc aluminate dehydration catalyst which has been prepared employing an approximate molar ratio of zinc oxide to alumina of one and which has been heated as in air for a sufficient time and at a sufficient temperature to form a catalytically active zinc aluminate suitable for said dehydration.

I claim:

1. The dehydration to an olefin of a dehydratable saturated alcohol which comprises subjecting the same to dehydrating conditions in the presence of a zinc aluminate dehydration catalyst having an approximate molar ratio of ZnO to Al$_2$O$_3$ of one, said catalyst having been heated in air for a sufficient time and at a sufficient temperature to form a catalytically active zinc aluminate suitable for said dehydration.

2. A process according to claim 1 wherein the alcohol contains from 2 to about 25 carbon atoms per molecule.

3. A process according to claim 2 wherein the alcohol is represented by the formula:

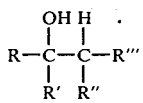

wherein each of R, R', R", and R'" is independently chosen from a group consisting of hydrogen, alkyl radicals, cycloalkyl radicals, said radicals contain from 1 to about 23 carbon atoms per radical, any of said alkyl or cycloalkyl radicals can contain aryl or substituted aryl radicals with the substituents being one or more or a mixture of alkyl or alkoxy radicals and with the limitation that said aryl or substituted aryl radicals must be located at least two carbon atoms from the alcohol oxygen, and any two of R, R', R", and R'" can be combined to form a mono- or bicyclic system with the limitation that any cyclic ring bearing an alcohol group must contain at least 4 carbon atoms in the ring.

4. A process according to claim 3 wherein the alcohol contains from 5 to about 25 carbon atoms per molecule and is represented by the formula:

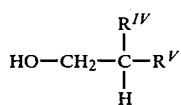

wherein each of $R^{IV}$ and $R^V$ is independently chosen from a group consisting of alkyl radicals containing from 1 to about 20 carbon atoms per radical and wherein $R^{IV}$ and $R^V$ can be taken together to form a mono- or bicyclic system having at least 4 carbon atoms in a ring bearing an alcohol group.

5. A process according to claim 1 wherein the alcohol is at least one selected from:

| ethanol | 1-hexadecanol | 2-methyl-1-pentanol |
|---|---|---|
| 1-propanol | 1-octadecanol | 2-ethyl-1-hexanol |
| 2-propanol | 1-eicosanol | 2-methyl-1-decanol |
| 1-butanol | 1-docosanol | 2-ethyl-1-octadecanol |
| 2-butanol | 1-pentacosanol | 2-methyl-1-eicosanol |
| 1-pentanol | cyclobutanol | 2-methyl-1-docosanol |

-continued

| 2-pentanol | cyclopentanol | cyclobutylmethanol |
|---|---|---|
| 3-pentanol | cyclohexanol | cyclopentylmethanol |
| 3-methyl-1-butanol | cyclooctanol | cyclohexylmethanol |
| 1-hexanol | cyclodocecanol | cyclotetradecylmethanol |
| 2-hexanol | cyclodocosanol | bicyclo[2.2.1]hept-2-ylmethanol |
| 3-hexanol | 4-methyl-2-pentanol | |
| 1-heptanol | 5,5-dimethyl-1-hexanol | bicyclo[2.2.2]oct-2-ylmethanol |
| 1-octanol | 5-phenyl-1-pentanol | |
| 2-octanol | 8-phenyl-2-octanol | |
| 1-nonanol | 2-methyl-2-pentanol | |
| 2-nonanol | 1-methyl-1-cyclohexanol | |
| 1-decanol | 2-methyl-1-cyclohexanol | |
| 1-undecanol | bicyclo[2.2.2]octan-2-ol | |
| 1-dodecanol | bicyclo[3.2.0]heptan-3-ol | |
| 1-tridecanol | bicyclo[2.2.1]heptan-2-ol | |
| 1-tetradecanol | 2-methyl-1-butanol | |
| 2-tetradecanol | 2-ethyl-1-butanol | |

6. A process according to claim 1 wherein the catalyst is prepared by mixing together ZnO and Al₂O₃ in a molar ratio in the approximate range 1/0.95 to 1/1.1.

7. A process according to claim 1 wherein the catalyst prior to use is calcined at a temperature in the approximate range 700–1400° C. for about 0.1 to about 30 hours.

8. A process according to claim 7 wherein the catalyst is calcined at a temperature in the approximate range 800–1200° C. for a period of time of from about 1 to about 20 hours.

9. A process according to claim 1 wherein the dehydration to olefin is affected at a temperature in the approximate range 200–600° C.

10. A process according to claim 9 wherein the dehydration is affected in the approximate range of from 250–450 ° C.

11. A process according to claim 1 wherein 2-methyl-1-butanol is converted to 2-methyl-1-butene.

12. A process according to claim 1 wherein the alcohol is 1-pentanol.

13. A process according to claim 1 wherein the alcohol is 2-pentanol.

14. A process according to claim 1 wherein the alcohol is 3-methyl-1-butanol.

15. A process according to claim 1 wherein the alcohol is cyclohexanol.

* * * * *